US010238599B2

(12) United States Patent
Miller et al.

(10) Patent No.: US 10,238,599 B2
(45) Date of Patent: *Mar. 26, 2019

(54) COMPOSITION AND METHOD FOR TREATING CONGENITAL CYTOMEGALOVIRUS INDUCED HEARING LOSS

(71) Applicant: The Regents of the University of Michigan, Ann Arbor, MI (US)

(72) Inventors: Josef M. Miller, Ann Arbor, MI (US); Glenn E. Green, Dexter, MI (US); Barry Sheldon Seifer, Ann Arbor, MI (US); Albert Park, Salt Lake City, UT (US); Ali Ahmed Almishaal, Alahsa-Hufof (SA); Phayvanh Phithaksounthone Sjogren, Salt Lake City, UT (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/714,445

(22) Filed: Sep. 25, 2017

(65) Prior Publication Data

US 2018/0008537 A1  Jan. 11, 2018

Related U.S. Application Data

(63) Continuation-in-part of application No. 14/847,178, filed on Sep. 8, 2015, now Pat. No. 9,770,433, which is a continuation-in-part of application No. 13/839,760, filed on Mar. 15, 2013, now Pat. No. 9,144,565, which is a continuation-in-part of application No. 13/679,224, filed on Nov. 16, 2012, now Pat. No. 8,927,528, which is a continuation-in-part of application No. 13/091,931, filed on Apr. 21, 2011, now Pat. No. 8,338,398, and a continuation-in-part of application No. 12/761,121, filed on Apr. 15, 2010, now Pat. No. 8,338,397, which is a continuation-in-part of application No. 11/623,888, filed on Jan. 17, 2007, now Pat. No. 7,951,845, said application No. 13/091,931 is a continuation of application No. 11/623,888.

(60) Provisional application No. 60/760,055, filed on Jan. 19, 2006.

(51) Int. Cl.
| A61K 33/06 | (2006.01) |
| A61K 31/355 | (2006.01) |
| A61K 31/60 | (2006.01) |
| A61K 31/07 | (2006.01) |
| A61K 31/375 | (2006.01) |
| A61K 31/245 | (2006.01) |
| A61K 9/00 | (2006.01) |
| A61K 31/015 | (2006.01) |
| A61K 45/06 | (2006.01) |
| A61K 31/05 | (2006.01) |
| A61K 31/341 | (2006.01) |
| A61K 31/58 | (2006.01) |
| A61K 31/585 | (2006.01) |
| A61K 33/00 | (2006.01) |
| A61P 27/16 | (2006.01) |
| A61P 31/22 | (2006.01) |

(52) U.S. Cl.
CPC .......... *A61K 9/0046* (2013.01); *A61K 9/0019* (2013.01); *A61K 31/015* (2013.01); *A61K 31/05* (2013.01); *A61K 31/07* (2013.01); *A61K 31/341* (2013.01); *A61K 31/355* (2013.01); *A61K 31/375* (2013.01); *A61K 31/58* (2013.01); *A61K 31/585* (2013.01); *A61K 33/00* (2013.01); *A61K 33/06* (2013.01); *A61K 45/06* (2013.01); *A61P 27/16* (2018.01); *A61P 31/22* (2018.01); *A61K 2300/00* (2013.01)

(58) Field of Classification Search
CPC ...... A61K 33/06; A61K 31/355; A61K 31/60; A61K 31/07; A61K 31/375; A61K 31/245
See application file for complete search history.

(56) References Cited

U.S. PATENT DOCUMENTS

| 5,597,585 A | 1/1997 | Williams et al. |
| 6,093,417 A | 7/2000 | Petrus |
| 6,177,434 B1 | 1/2001 | Kopke et al. |
| 6,265,386 B1 | 7/2001 | Campbell |

(Continued)

FOREIGN PATENT DOCUMENTS

| EP | 1258243 A1 | 11/2002 |
| WO | 9856761 A2 | 12/1998 |

(Continued)

OTHER PUBLICATIONS

Gutteridge et al., "Antioxidant protection and oxygen radical signaling. In: Gilbert, D.L, Colton, C.A., (Eds.), Reactive oxygen species in biological systems: An interdisciplinary approach", Kluwer Academic/Plenum Publishers, New York. 1999, pp. 189-218.

Halliwell, "Free Radicals in Biology and Medicine", 3rd Ed., Oxford Univ. Press (1999), Chapter 3—Antioxidant defences, pp. 105-245.

Haupt et al., "Therapeutic efficacy of magnesium in acoustic trauma in the guinea pig", ORL. J. Otorhinolaryngol. Relat. Spec. 65, 2003, pp. 134-139.

(Continued)

*Primary Examiner* — Sahar Javanmard
(74) *Attorney, Agent, or Firm* — Howard & Howard Attorneys PLLC

(57) ABSTRACT

A method of treating congenital cytomegalovirus (cCMV) induced hearing loss includes the step administering a composition to the mammal, wherein the composition consists essentially of a biologically effective amount of vitamin A, vitamin E, vitamin C, a vasodilator comprising magnesium, and, optionally, a withanolide, and/or resveratrol.

24 Claims, No Drawings

(56) References Cited

U.S. PATENT DOCUMENTS

| | | | |
|---|---|---|---|
| 6,288,106 | B1 | 9/2001 | Pearson et al. |
| 6,423,321 | B2 | 7/2002 | Tobinick |
| 6,524,619 | B2 | 2/2003 | Pearson et al. |
| 6,562,378 | B1 | 5/2003 | Chandra |
| 6,649,621 | B2 | 11/2003 | Kopke et al. |
| 6,660,297 | B2 | 12/2003 | Bartels et al. |
| 6,815,434 | B2 | 11/2004 | Kil et al. |
| 7,786,100 | B2 | 8/2010 | Miller et al. |
| 7,951,845 | B2 | 5/2011 | Miller et al. |
| 8,053,424 | B2 | 11/2011 | Miller et al. |
| 8,338,397 | B2 | 12/2012 | Miller |
| 8,338,398 | B2 | 12/2012 | Miller et al. |
| 8,927,528 | B2 | 1/2015 | Miller et al. |
| 9,144,565 | B2 | 9/2015 | Miller et al. |
| RE46,372 | E | 4/2017 | Miller et al. |
| 9,770,433 | B2 | 9/2017 | Miller et al. |
| 9,889,156 | B2 | 2/2018 | Miller et al. |
| 2002/0061870 | A1 | 5/2002 | Pearson et al. |
| 2003/0191064 | A1 | 10/2003 | Kopke |
| 2004/0033273 | A1 | 2/2004 | Patwardhan et al. |
| 2004/0096524 | A1 | 5/2004 | Nair et al. |
| 2004/0101560 | A1 | 5/2004 | Sawchuk et al. |
| 2004/0224012 | A1 | 11/2004 | Suvanprakom et al. |
| 2004/0247570 | A1 | 12/2004 | Miller et al. |
| 2004/0258781 | A1 | 12/2004 | Nair et al. |
| 2005/0013854 | A1 | 1/2005 | Mannino et al. |
| 2005/0070607 | A1 | 3/2005 | Andrus et al. |
| 2005/0107338 | A1 | 5/2005 | Seidman |
| 2015/0374659 | A1 | 12/2015 | Miller et al. |
| 2017/0065632 | A1 | 3/2017 | Miller et al. |

FOREIGN PATENT DOCUMENTS

| | | |
|---|---|---|
| WO | 0184961 A2 | 11/2001 |
| WO | 03030818 A2 | 4/2003 |
| WO | 2004000297 A1 | 12/2003 |
| WO | 2004016100 A2 | 2/2004 |
| WO | 2004037205 A2 | 5/2004 |
| WO | 2004050021 A2 | 6/2004 |

OTHER PUBLICATIONS

Haupt et al., Preventive magnesium supplement protects the inner ear against noise-induced impairment of blood flow and oxygenation in the guinea pig. Magnes. Res. 15, 2002, pp. 17-25.

Heinrich et al, "Ascorbic Acid Reduces Noise-Induced Nitric Oxide Production in the Guinea Pig Ear", Laryngoscope 118, The American Laryngological, Rhinological and Otological Society, Inc., May 2008, pp. 837-842.

Henderson et al., The role of antioxidants in protection from impulse noise. Ann. N. Y. Acad. Sci. 884, 1999, pp. 368-380.

Hight et al., "Noise-induced hearing loss in chinchillas pre-treated with glutathione monoethylester and R-PIA", Hear. Res. 179, 2003, pp. 21-32.

Hilgert et al., "Forty-six genes causing nonsyndomic hearing impairment: Which ones should be analyzed in DNA diagnostics?", Mutation Research 681, 2009, pp. 189-196.

Hilgert et al., "Phenotypic variability of patients homozygous for the GJB2 mutation 35delG cannot be explained by the influence of one major modifier gene", European Journal of Human Genetics, 2009, 17, pp. 517-524.

Hoffman et al., "Potentiation of ototoxicity by glutathione depletion", Ann Ototol Rhinol Laryngol 97, 1, 1988, pp. 36-41.

Hou et al., "Effects of alpha-tocopherol on noise-induced hearing loss in guinea pigs", Hear. Res. 179, 2003, pp. 1-8.

Hu et al., "R-phenylisopropyladenosine attenuates noise-induced hearing loss in the chinchilla". Hear. Res. 113, 1997, pp. 198-206.

Inoue et al., "ATP-sensitive K+ channel in the mitochondrial inner membrane", Letters to Nature, vol. 352, Jul. 18, 1991, pp. 244-247.

International Search Report, International Application No. PCT/US 07/01422, dated Mar. 4, 2008, 2 pages.

Ising et al., "Increased noise trauma in guinea pigs through magnesium deficiency", Arch. Otorhinolaryngol. 236, 1982, pp. 139-146.

Jackson et al., "Antioxidant strategies for post-noise hearing loss recovery, International Symposium—Pharmacologic Strategies for Prevention and Treatment of Hearing Loss and Tinnitus", Niagra Falls, Ottawa, Canada, 2005, 1 page.

Jacono et al., "Changes in cochlear antioxidant enzyme activity after sound conditioning and noise exposure in the chinchilla", Hear Res 117, 1998, pp. 31-38.

Joachims et al., "Antioxidants in treatment of idiopathic sudden hearing loss", Otol. Neurotol. 24, 2003, pp. 572-575.

Joachims et al., "Dependence of noise-induced hearing loss upon perilymph magnesium concentration", J. Acoust. Soc. Am. 74, 1983, pp. 104-108.

Joachims et al., "Oral magnesium supplementation as prophylaxis for noise-induced hearing loss: results of a double blind field study", Schriftenr. Ver. Wasser. Boden. Lufthyg. 88, 1993, pp. 511-516.

Jung et al., "Effects of Ginkgo biloba extract on the cochlear damage induced by local gentamicin installation in guinea pigs", J. Korean Med. Sci. 13, 1998, pp. 525-528.

Kalkanis et al., "Vitamin E reduces cisplatin ototoxicity", Laryngoscope 114, 2004, pp. 538-542.

Kelsell et al., "Connexin 26 mutations in hereditary non-syndromic sensorineural deafness", Letters to Nature, vol. 387, May 1997, pp. 80-83.

Kenna et al., "Audiologic phenotype and progression in GJB2 (Connexin 26) hearing loss", Arch Otolaryngol Head Neck Surg. 36(1), 2010, pp. 81-87.

Kikuchi et al., "Gap junction systems in the mammalian cochlea", Brain Research Reviews 32, 2000, pp. 163-166.

Knight, "Popping pill may prevent hearing loss", [Online] http://www.newscientist.com/article.ns?id=dn2666 (posted Aug. 13, 2002; verified Feb. 25, 2005), 2 pages.

Kopke et al., "A radical demise-Toxins and trauma share common pathways in hair cell death", Ann N Y Acad Sci 884, 1999, pp. 171-191.

Kopke et al., "Candidate's thesis: Enhancing intrinsic cochlear stress defenses to reduce noise-induced hearing loss", Laryngoscope 112, 2002, pp. 1515-1532.

Kopke et al., "Reduction of noise-induced hearing loss using L-NAC and salicylate in the chinchilla", Hear. Res. 149, 2000, pp. 138-146.

Kopke, "NAC for Noise: From the bench top to the clinic," International Symposium—Pharmacologic Strategies for Prevention and Treatment of Hearing Loss and Tinnitus, Niagra Falls, Ottawa, Canada, 2005, 1 page.

Kujawa et al., "Acceleration of Age-Related Hearing Loss by Early Noise Exposure: Evidence of a Misspent Youth," Journal of Neuro., Feb. 15, 2006, 26(7), pp. 2115-2123.

Kujawa, "Adding insult to injury: Noise-induced and age-related hearing loss interactions," International Symposium—Pharmacologic Strategies for Prevention and Treatment of Hearing Loss and Tinnitus, Niagra Falls, Ottawa, Canada, 2005, 1 page.

Kulawiak et al., "BK channel openers inhibit ROS production of isolated rat brain mitochondria", Experimental Neurology 212, 2008, pp. 543-547.

Kwon et al., "Sodium salicylate inhibits expression of COX-2 through suppression of ERK and subsequent NF-kappaB activation in rat ventricular cardiomyocytes", Arch Pharm Res 26, 2003, pp. 545-553.

Labdiet, "PicoLab Laboratory Rodent Diet", Jan. 9, 2014, 1 page.

Laurikainen et al., "Betahistine Effects on Cochlear Blood Flow: From the Laboratory to the Clinic", Acta Otolaryngol, Supp. 544, 2000, pp. 5-7.

Laurikainen et al., "Non-Specific Effect of Beettahistine on Cochlear Electrophysiology in Guinea Pig", Acta Otolayngol (Stockh), Supp. 529, 1997, pp. 77-79.

Lautermann et al., "Glutathione protection against gentamicin ototoxicity depends on nutritional status", Hear Res 86, 1995, pp. 15-24.

(56) References Cited

OTHER PUBLICATIONS

Le Prell et al., "Electromotile hearing: Acoustic tones mask psychophysical response to high-frequency electrical stimulation of intact guinea pig cochlea", J, Acoust. Soc. Am. 120 (6), Dec. 2006, pp. 3889-3900.
Le Prell et al., "Free Radical Scavengers Vitamins A, C and E Plus Magnesium Reduce Noise Trauma", Free Radical Biology & Medicine 42, 2007, pp. 1454-1463.
Le Prell et al., "Mechanisms of Noise-Induced Hearing Loss Indicate Multiple Methods of Prevention", Hearing Research 226, Elsevier B.V., 2007, pp. 22-43.
Le Prell et al., Pathways for protection from noise induced hearing loss, Noise Health 5, 2003, pp. 1-17.
Li et al., "Salicylate protects hearing and kidney function from cisplatin toxicity without compromising its oncolytic action",Lab Invest 82, 2002, pp. 585-596.
Lohle, "The influence of a chronic vitamin A deficiency on the acoustic sensory cells and the ganglion spirale cochleae of the rat", An electron microscope study. Arch. Otorhinolaryngol. 229, 1980, pp. 45-53.
Lohle, "Ultrastructural changes in the organ of Corti and in the ganglion spiral cochleae after vitamin A deficiency", Pathol. Res. Pract. 179, 1985, pp. 560-567.
Lopez-Gonzalez et al., "Ototoxicity caused by cisplatin is ameliorated by melatonin and other antioxidants", J. Pineal Res. 28, 2000, pp. 73-80.
Martinez et al., "Gap-Junction Channel Dysfunction in Deafness and Hearing Loss," Antioxidants & Redox Signaling, vol. 11, No. 2, 2009, pp. 309-372.
McFadden et al., Dietary Vitamin C Supplementation Reduces Noise-Induced Hearing Loss in Guinea Pigs, Hearing Research 202, 2005, pp. 200-208.
Miller et al., "8-iso-prostaglandin F(2alpha), a product of noise exposure, reduces inner ear blood flow", Audiol. Neurootol. 8, 2003, pp. 207-221.
Miller et al., "Interactive Effects of Aging with Noise Induced Hearing Loss", Scand. Audiol, 27, 1998, pp. 53-61.
Miller et al., "Mechanisms and Prevention of Noise-Induced Hearling Loss", Otol Jpn, 16(2), 2006, p. 139.
Minami et al., "Creatine and Tempol Attenuate Noise-Induced Hearing Loss", Brain Res. May 7, 2007, pp. 1-13.
Morton et al., "Newborn Hearing Screening—A Silent Revolution", New Engl J Med 354, 2006, pp. 2151-2164.
Nageris et al., "Magnesium treatment for sudden hearing loss", Ann. Otol. Rhinol. Laryngol. 113, 2004, pp. 672-675.
Nang et al., "Tanshinone (Salviae miltiorrhizae Extract) Preparations Attenuate Aminoglycoside-Induced Free Radical Formation in Vitro and Ototoxicity in Vivo", Antimicrobial Agents and Chemotherapy, Jun. 2003, vol. 47, No. 5, pp. 1836-1841.
Nangemann, "K+ Cycling and Its Regulation in the Cochlea and the Vestibular Labyrinth", Audiol Neurootol 7, 2002, pp. 199-205.
Nangemann, "K+ Cycling and the endocochlear potential", Hearing Research 165, 2002, pp. 1-9.
Nickel et al., "Gap junctions and connexins in the inner ear: their roles in homeostasis and deafness", Current Opinion in Otolryngology & head and Neck Surgery 16, 2008, pp. 452-457.
Niki et al., "Interaction among Vitamin C, Vitamin E, and Beta-Carotene .LAMBDA.1-3", Am J Clin Nutr 62(suppl), 1995, pp. 1322S-1326S.
Niki, "Action of ascorbic acid as a scavenger of active and stable oxygen radicals", Am J Clin Nutr 54, 1991, pp. 1119S-1124S.
Niki, "Interaction of Ascorbate and Alpha-Tocophpperol", Department of Reaction Chemistry, Faculty of Engineering, University of Tokyo, pp. 186-199.
Niki, "Lipid antioxidants: How they may act in biological systems", Br. J. Cancer (1987), 55, Suppl. VIII, pp. 153-157.
Ohinata et al., "Glutathione limits noise-induced hearing loss", Hearing Research 146, 2000, pp. 28-34.
Ohinata et al., "Protection from noise-induced lipid peroxidation and hair cell loss in the cochlea", Brain Res. 966, 2003, pp. 265-273.
Ohinata, "Intense noise induces formation of vasoactive lipid peroxidation products in the cochlea", Brain Res. 878, 2000, pp. 163-173.
Ohlemiller et al., "Early Elevation of Cochlear Reactive Oxygen Species following Noise Exposure", Audiol Neurootol 4, 1999, pp. 229-236.
Oleinick et al., "The Photobiology of Photodynamic Therapy: Cellular Targets and Mechanisms", Radiation Research 150 (Suppl.), 1998, pp. S146-S156.
Omenn et al., "Effects of a combination of beta carotene and vitamin A on lung cancer and cardiovascular disease", N. Engl. J. Med. 334, 1996, pp. 1150-1155.
Perlman et al., "Cochlear blood flow and acoustic trauma", Acta Otolaryngol. (Stockh). 54, 1962, pp. 99-119.
Pierson et al., "Prophylaxis of kanamycin-induced ototoxicity by a radioprotectant", Hear Res 4, 1981, pp. 79-87.
Piwonska et al., "Differential Distribution of Ca 2+—Activated Potassium Channel Beta 4 Subunit in Rat Brain: Immunolocalization in Neuronal Mitochondria", Neuroscience 153, 2008, pp. 446-460.
Population Reference Bureau, "Human Population: Urbanization, Largest Urban Agglomerations, 1975, 2000, 2025, Teachers Guide: Discussion Guide", originally downloaded from http://www.prb.org/Publications/Less-Plans/HumanPopulation/Urbanization.a-spx on Aug. 27, 2016.
Priuska et al., "Formation of free radicals by gentamicin and iron and evidence for an iron-gentamicin complex", Biochem Pharmacol 50(11), 1995, pp. 1749-1752.
Rabinowitz et al., "Antioxidant status and hearing function in noise-exposed workers", Hear. Res. 173, 2002, pp. 164-171.
Romeo, "The Therapeutic Effect of Vitamins A and E in Neurosensory Hearing Loss", [Italian] Journal Article—Acta Vitamininol. Enzymol. 7 Suppl, 1985, pp. 85-92, 1 Page English Abstract from OVID Search Results.
Rybak et al., "Ototoxicity", Kidney International 72, 2007, pp. 931-935.
Ryter et al., "Comprehensive Invited Review: Mechanisms of Cell Death in Oxidative Stress", Antioxidants & Redox Signaling, vol. 9, No. 1, 2007, pp. 49-89.
Schact, "Antioxidant therapy attenuates aminoglycoside-induced hearing loss", Ann. N. Y. Acad. Sci. 884, 1999, pp. 125-130.
Schafer et al., "Comparing Beta-Carotene, Vitamin E and Nitric Oxide as Membrane Antioxidants", Biol. Chem. vol. 383, Mar./Apr. 2002, pp. 671-681.
Scheibe et al. "Preventive effect of magnesium supplement on noise-induced hearing loss in the guinea pig", Eur. Arch. Otorhinolaryngol. 257, 2000, pp. 10-16.
Scheibe et al. "Therapeutic effect of parenteral magnesium on noise-induced hearing loss in the guinea pig", Magnes. Res. 15, 2002, pp. 27-36.
Scheibe et al., "Preventive magnesium supplement reduces ischemia-induced hearing loss and blood viscosity in the guinea pig", Eur Arch Otorhinolaryngol 257, 2000, pp. 355-361.
Scheibe et al., "Total magnesium concentrations of perilymph, cerebrospinal fluid and blood in guinea pigs fed different magnesium-containing diets", Eur. Arch. Otorhinolaryngol. 256, 1999, pp. 215-219.
Schneider et al., "Gingko biloba (Rokan) therapy in tinnitus patients and measurable interactions between tinnitus and vestibular disturbances", Int. Tinnitus J. 6, 2000, pp. 56-62.
Seidman et al., "Effects of resveratrol on acoustic trauma", Otolaryngol. Head Neck Surg. 129, 2002, pp. 463-470.
Seidman, "Effects of dietary restriction and antioxidants on presbyacusis", Laryngoscope 110, 2000, pp. 27-38.
Sergi et al., "The role of antioxidants in protection from ototoxic drugs", Acta Otolaryngol. Suppl. (Stockh), 2004, pp. 42-45.
Sha et al., "Aspirin to prevent gentamicin-induced hearing loss", N Engl J Med 354(17), 2006, pp. 1856-1857.
Sha et al., "Formation of reactive oxygen species following bioactivation of gentamicin", Free Rad Biol Med 26(3-4), 1999, pp. 341-347.
Sha et al., "Salicylate attenuates gentamicin-induced ototoxicity", Lab Invest 79, pp. 807-813.

(56) References Cited

OTHER PUBLICATIONS

Shoji et al., "Differential Protective Effects of Neurotrophins in the Attenuation of Noise-Induced Hair Cell Loss", Hearing Research 146, 2000, pp. 134-142.
Siemen et al., "Ca 2+—Activated K Channel of the BK-Type in the Inner Mitochondrial Membrane of a Human Glioma Cell Line", Biochemical and Biophysical Research Communications, 257, 1999, pp. 549-554.
Soares et al., "Sequestering Ability of Butylated Hydroxytoluene, Propyl Gallate, Resveratrol, and Vitamins C and E against ABTS, DPPH, and Hydroxul Free Radicals in Chemical and Biological Systems", J. Agric. Food Chem. 51, 2003, pp. 1077-1080.
Song et al., "Variable efficacy of radical scavengers and iron chelators to attenuate gentamicin ototoxicity in guinea in pig in vivo", Hear Res 94, 1996, pp. 87-93.
Song et al.,"Iron chelators protect from aminoglycosideinduced cochlea- and vestibulotoxicity in guinea pig", Free Radic. Biol. Med. 25, 1998, pp. 189-195.
Szabo et al., "A Novel Potassium Channel in Lymphocyte Mitochondria", The Journal of Biological Chemistry, vol. 280, No. 13, Apr. 1, 2005, pp. 12790-12798.
Takemura et al., "Direct Inner Ear Infusion of Dexamethasone Attenuates Noise-Induced Trauma in Guinea Pig", Hearing Research 196, 2004, pp. 58-68.
Takumida et al., "Radical scavengers for Meniere's disease after failure of conventional therapy: a pilot study", Acta Otolaryngol. (Stockh). 123, 2003, pp. 697-703.
Tanswell et al., "Antioxidant therapy in critical care medicine", New Horizons 3, 1995, pp. 330-341, 1 page abstract from OVID:Search Results on Apr. 22, 2006.
Teranishi et al., "Effects of alpha-tocopherol on cisplatin-induced ototoxicity in guinea pigs", Hear. Res. 151, 2011, pp. 61-70.
The Alpha-Tocopherol, Beta Carotene Cancer Prevention Study Group. The effect of vitamin E and beta carotene on the incidence of lung cancer and other cancers in male smokers. N. Engl. J. Med. 330, 1994, pp. 1029-1035.
Tsuchihashi et al., "Action of Beta-Carotene as an Antioxidant against Lipid Peroxidation", Archives of Biochemistry and Biophysics, vol. 323, No. 1, Oct. 20, 1995, pp. 137-147.
U.S. Appl. No. 15/272,981, filed Sep. 22, 2016.
Usami et al., "Differential cellular distribution of glutathione—an endogenous antioxidant—in the guinea pig inner ear", Brain Res. 743, 1996, pp. 337-340.
Wang et al., "Bcl-XL disrupts death-inducing signal complex formation in plasma membrane induced by hypoxia/reoxygenation", The FASEB Journal, Research Communication, pp. 1826-1833.
Wang et al., "Hepatocyte Growth Factor Protects against Hypoxia/Reoxygenation-induced Apoptosis in Endothelial Cells", The Journal of Biological Chemistry, vol. 279, No. 7, Feb. 13, 2004, pp. 5237-5243.
Watanabe et al., "Acoustic stimulation promotes the expression of inducible nitric oxide synthase in the vestibule of guinea pigs", Acta Otolaryngol. Suppl. 553: (Stockh)., 2004, pp. 54-57.
Weijl et al., "Supplementation with antioxidant micronutrients and chemotherapy-induced toxicity in cancer patients treated with cisplatin-based chemotherapy: a randomised, double-blind, placebo-controlled study", Eur. J. Cancer 40, 2004, pp. 1713-1723.
World Health Organization, "Hearing Loss Due to Recreational Exposure to Loud Sounds: A Review", 2015, pp. 1-32.
World Health Organization, "WHO Global Estimates on Prevalence of Hearing Loss—Mortality and Burden of Diseases and Prevention of Blindness and Deafness", 2012, 15 pages.
Yamashita et al., "Post-exposure treatment attenuates noise-induced hearing loss", Neuroscience, 134, 2005, pp. 633-642.
Yamashita, et al., "Delayed production of free radicals following noise exposure", Brain Res 1019, 2004, pp. 201-209.
Yamasoba et al., "Attenuation of Cochlear Damage From Noise Trauma by an Iron Chelator, a Free Radical Scavenger and Glial Cell Line-Derived Neurotrophic Factor in Vivo", Brain Research 815, 1999, pp. 317-325.
Yamasoba et al., "Influence of intense sound exposure on glutathione synthesis in the cochlea", Brain Research 804, 1998, pp. 72-78.
Yamasoba et al., "Role of glutathione in protection against noise-induced hearing loss", Brain Res. 784, 1998, pp. 82-90.
Yamasoba, T., "Oxidative Stress in Applied Basic Research and Clinical Practice, Oxidative Stress and Age-Related Hearing Loss, Part VI—Interventions to Prevent Age-Related Hearing Loss", Free Radicals in ENT Pathology, Eds.: Miller, J., Le Press,C and Rybak, L., Humana Press, 2015, pp. 335-349.
Yu, "Regulation and critical role of potassium homeostasis in apoptosis", Progress in Neurobiology 70, 2003, pp. 363-386.
Zhao et la., "Oxidative damage pathways in relation to normal tissue injury", The British Journal of Radiology, 80, 2007, pp. S23-S31.
A Randomized, Placebo-Controlled, Clinical Trial of High-Dose Supplementation With Vitamins C and E, Beta Carotene and Zinc for Age-Related Degeneration and Vision Loss, Arch Ophthalmol, 119(10), Oct. 2001, pp. 1417-1436.
Abaamrane et al., "Long-term Administration of Magnesium After Acoustic Trauma Caused by Gunshot Noise in Guinea Pigs", Hearing Research 247, 2009, pp. 137-145.
Abstract of Aamisalo et al., "Apoptosis in Auditory Brainstem Neurons after a Severe Noise Trauma of the Organ of Corti: Intracochlear GDNF treatment Reduces the Number of Apoptotic Cells", ORL Original Paper, Apr. 2, 2000, No. 62, 1 page.
Abstract of Fetoni et al., "Protective Effects of x-Tocopherol Against Gentamicin-induced Oto-vestibula Toxicity: An Experimental Study", Acta Otolaryngol, 2003, No. 123, 1 page.
Abstract of Laurikainen et al., "The Vascular Mechanism of Action of Betahistine in the Inner Ear of the Guinea Pig", Eur Arch Otorhinolaryngol, 1998, No. 255, 1 page.
Abstract of McFadden et al., "M40403, a superoxide dismutase minetic, protects cochlear hair cells from gentamicin, out not cisplatin toxicity", Science Direct, Toxicology and Applied Pharmacology, 2003, No. 186, 1 page.
Agarwal et al., "Phospholipase Activation Triggers Apoptosis in Photosensitized Mouse Lymphoma Cells", Cancer Research 53, Dec. 15, 1993, pp. 5897-5902.
Agrawal, Y., et al., "Prevalence of Hearing Loss and Differences by Demographic Characteristics Among U.S. Adults", Data from the National Health and Nutrition Examination Survey, 1999-2004. Arch Intern Med. 2008; 168, pp. 1522-1530.
Ahn et al., Anti-Apoptotic Role of Retinoic Acid in the Inner Ear of Noise-Exposed Mice, Biochemical and Biophysical Research Commmunications 335, 2005, pp. 485-490.
Altura et al., "Noise-induced hypertension and magnesium in rats: relationship to microcirculation and calcium", J Appl Physiol, 1992, 72, pp. 194-202.
Altura et al., Role of Mg ions in contractility of blood vessels and skeletal muscles. Magnesium-B 1a, 1981, pp. 102-114.
Ames et al., "Oxidants, antioxidants, and the degenerative diseases of aging", Proc. Natl. Acad. Sci. USA, Sep. 1993, vol. 90, pp. 7915-7922.
Aoshiba et al., "Acute cigarette smoke exposure induces apoptosis of alveolar macrophages", Am J Physiol Lung sell Mol Physiol 281, 2001, pp. L1392-L1401.
Attias et al, Oral magnesium intake reduces permanent hearing loss induced by noise exposure. Am. J. Otolaryngol. 15, 2004, pp. 26-32.
Attias et al., "Reduction in Noise-Induced Temporary Threshold Shift in Humans Following Oral Magnesium Intake", Clinical Otolaryngology 29, Blackwell Publishing Ltd, 2004, pp. 635-641.
Attias et al., "Preventing noise induced otoacoustic emission loss by increasing magnesium (Mg2+) intake in guinea-pigs." J. Basic Clin. Physiol. Pharmacol. 14, 2003, pp. 119-136.
Balavoine et al., "Peroxynitrite scavenging by different antioxidants. Part I: Convenient Assay", Nitric Oxide 3, 1999, pp. 40-54.
Bednarczyk et al., "New Properties of mitochondrial ATP-regulated potassium channels", J. Bionerg Biomembr, 2008, 40, pp. 325-335.
Bertolaso et al., "Apoptosis in the OC-k3 immortalized cell line treated with different agents", Audiology 40, 2001, pp. 327-335.
Biesalski, et al., "Vitamin A deficiency increases noise susceptibility in guinea pigs", J. Nutr. 120, 1990, pp. 726-737.
Bock et al., "Effects of N-acetylcysteine on kanamycin ototoxicity in the guinea pig", Hear Res 9, 1983, pp. 255-262.

(56) References Cited

OTHER PUBLICATIONS

Boland et al., "Pre- and post-treatment with pirlindole and dehydropirlindole protects cultured brain cells against nitric oxide-induced death", Eur J Pharmacol 466, 2003, pp. 21-30.

Branis et al., "Effect of Ascorbic Acid on the Numerical Hair Cell Loss in Noise Exposed Guinea Pigs", Hearing Research 33, Elsevier Science Publishers B.V., 1988, pp. 137-140.

Budinger et al., "Hyperoxia-induced Apoptosis Does Not Require Mitochondrial Reactive Oxygen Species and Is Regulated by Bcl-2 Proteins", The Journal of Biological Chemistry, vol. 277, No. 18, May 3, 2002, pp. 15654-15660.

Burton et al., "Is Vitamin E the Only Lipid-Soluble, Chain-Breaking Antioxidant in Human Blood Plasma and Erythrocyte Membranes?", Archives of Biochemistry and Biophysics, vol. 221, No. 1, Feb. 15, 1983, pp. 281-290.

Carnevali et al., "Cigarette smoke extract induced oxidative stress and apoptosis in human lung fibroblasts", Am J Physiol Lung Cell Mol Physiol 284, 2003, pp. L955-L963.

Cevette et al., "Magnesium and hearing", J. Am. Acad. Audiol. 14, 2003, pp. 202-212.

Chae et al., "Salicylate regulates COX-2 expression through ERK and subsequent NF-kappaB activation in osteoblasts", Immunopharmacol Immunotoxicol 26, 2004, pp. 75-91.

Chan et al., "Connexin-26-associated deafness: phenotypic variability and progression of hearing loss", Genet Med. 2010, 12, pp. 174-181.

Cohen-Salmon et al., "Targeting Ablation of Connexin26 in the Inner Ear Epithelial Gap Junction Network Causes Hearing Impairment and Cell Death", Current Biology, vol. 12, Jul. 9, 2002, pp. 1106-1111.

Constricted Blood Vessels, downloaded from http://www.menieres.org/forums/NonCGI/Forum1/HTML/003686.html, 1 page.

Coyle et al., "Pendred syndrome (goitre and sensorineural hearing loss) maps to chromosome 7 in the region containing the nonsyndromic deafness gene DFNB4", Apr. 1996, Nature Genetics, vol. 12, pp. 421-423.

Cryns et al., "A genotype-phenotype correlation for GJB2 (connexin 26) deafness", J Med Genet 2004, 41, pp. 147-154.

Diamond et al., Ginkgo biloba extract: mechanisms and clinical indications. Arch. Phys. Med. Rehabil. 81, 2000, pp. 668-678.

Didier et al., "Effects of Ginkgo biloba extract (EGb 761) on cochlear vasculature in the guinea pig: morphometric measurements and laser Doppler flowmetry", Eur. Arch. Otorhinolaryngol. 253, 1996, pp. 25-30.

Duan et al., "Dose and time-dependent protection of the antioxidant N-L-acetylcysteine against impulse noise trauma", Hear. Res. 192, 2004 pp. 1-9.

Eliseev et al., "Bcl-2 and tBid proteins counter-regulate mitochondrial potassium transport", Biochimica et Biophysica Acta 1604, 2003, pp. 1-5.

Evans et al., "Free radicals and hearing. Cause, consequence, and criteria", Ann. N. Y. Acad. Sci. 884, 1999, pp. 19-40.

Fetoni et al., Alpha-Tocopherol protective effects on gentamicin ototoxicity: an experimental study. Int J Audiol 43, 2004, pp. 166-171.

Fischer et al., "Protection of the Cochlea by Ascorbic Acid in Noise Trauma", HNO 57(4), Apr. 2009, pp. 339-344 and English language abstract for Fischer et al., "Protection of the Cochlea by Ascorbic Acid in Noise Trauma", HNO 57 (4), Apr. 2009,pp. 339-344.

Floyd, "Antioxidants, oxidative stress, and degenerative neurological disorders", Proc Soc Exp Biol Med 222, 1999, pp. 236-245.

Forge et al., "Aminoglycoside Antibiotics", Audiol Neurootol 5, 2000, pp. 3-22.

Garetz et al., "Sulphydryl compounds and antioxidants inhibit cytotoxicity to outer hair cells of a gentamicin metabolite in vitro", Hear Res 77, 1994, pp. 75-80.

Godar et al., "Spectral Dependence of UV-Induced Immediate and Delayed Apoptosis: The Role of Membrane and DNA Damage", Photochemistry and Photobiology, vol. 62, No. 1, 1995, pp. 108-113.

Godar, "UVA1 Radiation Triggers Two Different Final Apoptotic Pathways", The Society for Investigative Dermatology Inc., 1999, pp. 3-12.

Gordin et al., Magnesium: a new therapy for idiopathic sudden sensorineural hearing loss. Otol. Neurotol. 23, 2002, pp. 447-451.

Green et al., "Audiological Manifestations and Features of Connexin 26 Deafness", Aud Med. 2003,1, pp. 5-11.

Green et al., "Genetic testing to identify deaf newborns", JAMA. 284, 2000, p. 1245.

Green et al., "Presentation, Hearing Improvement on a CEMg in a Child with Connexin 26 Hearing Loss", Feb. 2011 (University of Michigan, University of Florida), 5 pages.

Gunther et al., "Biochemical mechanisms affecting susceptibility to noise-induced hearing loss", Am. J. Otol. 10, 1989, pp. 36-41.

COMPOSITION AND METHOD FOR TREATING CONGENITAL CYTOMEGALOVIRUS INDUCED HEARING LOSS

RELATED APPLICATIONS

This patent application is a continuation-in-part of U.S. patent application Ser. No. 14/847,178 filed on Sep. 8, 2015. U.S. patent application Ser. No. 14/847,178 is a continuation-in-part of U.S. patent application Ser. No. 13/839,760 filed on Mar. 15, 2013, which is now U.S. Pat. No. 9,144,565. U.S. patent application Ser. No. 13/839,760 is a continuation-in-part of U.S. patent application Ser. No. 13/679,224 filed on Nov. 16, 2012, which is now U.S. Pat. No. 8,927,528. U.S. patent application Ser. No. 13/679,224 is a continuation-in-part of U.S. patent application Ser. No. 12/761,121 filed on Apr. 15, 2010, which is now U.S. Pat. No. 8,338,397. U.S. patent application Ser. No. 12/761,121 is a continuation-in-part of U.S. patent application Ser. No. 11/623,888 filed on Jan. 17, 2007, which is now U.S. Pat. No. 7,951,845. U.S. patent application Ser. No. 11/623,888 claims priority to and all advantages of U.S. Provisional Patent Application No. 60/760,055, filed on Jan. 19, 2006. U.S. patent application Ser. No. 13/679,224 is also a continuation-in-part of U.S. patent application Ser. No. 13/091,931 filed on Apr. 21, 2011, which is now U.S. Pat. No. 8,338,398. U.S. patent application Ser. No. 13/091,931 is a continuation of U.S. patent application Ser. No. 11/623,888 filed on Jan. 17, 2007, which is now U.S. Pat. No. 7,951,845. U.S. patent application Ser. No. 11/623,888 claims priority to and all advantages of U.S. Provisional Patent App. Ser. No. 60/760,055, filed on Jan. 19, 2006.

GOVERNMENT LICENSE RIGHTS

This disclosure was made with government support under DC004058 awarded by the National Institutes of Health. The government has certain rights in the disclosure.

BACKGROUND OF THE DISCLOSURE

Field of the Disclosure

The present disclosure generally relates to method for treating congenital cytomegalovirus (cCMV) induced hearing loss. More specifically, the method includes administering a composition to the mammal, wherein the composition consists essentially of a biologically effective amount of vitamin A, vitamin E, vitamin C, a vasodilator comprising magnesium, and, optionally, a withanolide, and/or resveratrol.

Description of the Related Art

Congenital cytomegalovirus (cCMV) is the most common infectious cause of sensorineural hearing loss (SNHL). With a prevalence of approximately 0.5%, it is estimated that 20,000 congenitally infected neonates are born in the U.S. annually. Almost 400 children die each year from this disease, and approximately 7,000 develop permanent disabilities. The most common permanent disability is hearing loss. It is estimated to account for at least 20% of SNHL in young children. More children are affected by cCMV than by other, better-known childhood conditions, such as Down syndrome, fetal alcohol syndrome, and spina bifida. This hearing loss has detrimental effects on speech and language development and incurs the major cost associated with cCMV infection, which has been estimated to be $4 billion a year.

Unfortunately, there is no effective treatment for cCMV-induced SNHL. A vaccine for cCMV infection is still lacking. Ganciclovir or its oral form, valganciclovir, may attenuate the progressive nature of cCMV-induced hearing loss, but causes neutropenia, potential infertility and teratogenesis. Accordingly, there remain opportunities to develop effective methods of treating various types and causes of cCMV. There is also an opportunity to provide a composition for treating cCMV induced SNHLs.

SUMMARY OF THE DISCLOSURE

The subject disclosure provides a method of treating congenital cytomegalovirus induced hearing loss that includes the step administering a composition to the mammal, wherein the composition consists essentially of a biologically effective amount of vitamin A, vitamin E, vitamin C, a vasodilator comprising magnesium, and, optionally, a withanolide, and/or resveratrol.

DETAILED DESCRIPTION

A composition for treating congenital cytomegalovirus induced hearing loss includes components that may function through different biological mechanisms to provide an additive effect that is equal to or greater than a sum of the effect of the individual components. The composition is typically used for treating cCMV induced hearing loss, such as cCMV-induced SNHL, or preventing future progressive hearing loss. Children with initial hearing loss and cCMV have a greater than 50% chance of developing future worsening hearing. The composition may also be used as a prophylaxis in those with normal hearing and cCMV. The risk for a cCMV infected individual with initial normal hearing is approximately 10%. There is a great need to have novel agents that can prevent the development of future hearing loss in these individuals.

A method in accordance with the instant disclosure includes the step of administering a composition to a mammal that includes components that function through different biological mechanisms. In the method, the composition is typically used for treating hearing loss resulting from a cCMV infection to the inner ear of a mammal.

It has been found that one result of cCMV is that excessive free radicals form in the cochlea. The free radicals damage sensitive structures, such as hair cells, within the ear and can initiate processes that can lead to hearing loss. Vasoconstriction also occurs as a result of this infection, which leads to decreased blood flow to the inner ear and causes cell death and vascular degeneration It has been found that the underlying cause of free radical formation mediates cCMV induced hearing loss in a mouse model. Specifically, the transcription factor Nrf2 is a key regulator of several detoxifying and antioxidant genes and is activated in response to oxidative and electrophilic stress may be an important pathway in cCMV mediated hearing loss.

By removing/eliminating excess free radicals antioxidants may restore auditory function. Antioxidants act through a variety of mechanisms. The at least one scavenger of singlet oxygen and the donor antioxidant are two different classes of antioxidants that act through different mechanisms. The third antioxidant, while typically a scavenger of singlet oxygen, may be a different antioxidant that acts through a different mechanism. Scavengers of singlet oxygen reduce free radicals that contribute to inner ear pathology and thus to cCMV induced hearing loss. More specifically, by reducing free radicals, the scavengers of singlet oxygen prevent, among other damaging effects, the singlet oxygen from reacting with lipids to form lipid hydroperoxides. Lipid hydroperoxides may also play a role in causing cCMV induced hearing loss.

Even within the class of scavengers of singlet oxygen, it is believed that various antioxidants react at different sites within the body, and in particular, within cells to attenuate free radical formation. For example, one of the scavengers of singlet oxygen is typically vitamin A. In various non-limiting embodiments described herein, the terminology Vitamin A and beta-carotene may be used interchangeably. However, these embodiments in no way limit this disclosure. Vitamin A is a generic term that captures a number of molecules with a biological activity of retinol or carotenoids. Primary dietary forms of vitamin A/retinol include retinol esters and beta-carotene. The beta-carotene is made up of a polyene chain of 11 conjugated double bonds with methyl branches spaced along the polyene chain, capped at both ends by cyclohexenyl rings with 1,1,5-trimethyl substitution. Other forms of vitamin A include xanxthophylls, astaxanthin, canthxanxin, lutein, and zeaxanthin, which include a backbone of beta-carotene with hydroxyl and/or carbonyl substitution on one or more of the cyclohexenyl rings. For purposes of the subject disclosure, the vitamin A is typically present as beta-carotene. Beta-carotene is a powerful scavenger of singlet oxygen, as well as nitric oxide and peroxynitrite, and may also scavenge lipid peroxyl radicals within a lipophilic compartment of a mitochondrial membrane. Beta-carotene is an excellent scavenger of free radicals under normal physiological conditions present in most tissues.

In addition to vitamin A, other scavengers of singlet oxygen may also be present in the composition of the subject disclosure. For example, another scavenger of singlet oxygen that may be present is resveratrol. Resveratrol is more efficient at scavenging hydroxyl radicals than vitamin C, and the addition of resveratrol to the vitamins A may have additive effects.

The at least one scavenger of singlet oxygen may be present in the composition in a biologically effective amount. For purposes of the subject disclosure, the biologically effective amount may be further defined as an amount that is sufficient to produce an additive effect in a reduction in stress induced threshold shift or cCMV induced hearing loss when used in combination with other antioxidants and the magnesium. Additive effect, as used herein, refers to an effect that is equal to or greater than a sum of the effects of the individual components. In order to produce additive effect and the reduction in threshold shift or cCMV induced hearing loss, the at least one scavenger of singlet oxygen is typically present in the composition in a total amount of at least 830 international units (IU), more typically from 830 to 120,000 IU, most typically from about 2,100 to 70,000 IU for an adult dosage.

The amount of the vitamin A present in the composition is dependent upon the form of vitamin A that is used. For example, in one embodiment, vitamin A is present as retinol in an amount of at least 830 IU, more typically from 830 to 10,000 IU, more typically from 2,100 to 10,000 IU, most typically from 2,100 to 8,000 IU. As known in the art, a conversion of IU to weight for vitamin A (as retinol) is 3.33 IU/µg. Thus, at least 830 international units (IU) of vitamin A (as retinol) is equivalent to at least 0.25 mg of vitamin A, from 830 to 10,000 IU of vitamin A (as retinol) is equivalent to from 0.25 to 3 mg of vitamin A, and from 2,100 to 8,000 IU of vitamin A (as retinol) is equivalent to from 0.63 to 2.4 mg vitamin A.

Alternatively, the vitamin A may be present in the composition as beta-carotene, as opposed to retinol. The retinol activity equivalents (RAE) for retinol conversion to beta-carotene, which is a pro-vitamin A carotenoid, is 1 mg to 12 mg. In terms of conversion of the amounts set forth above for the vitamin A present in the composition as retinol to the vitamin A present in the composition as beta-carotene, in one example, a total amount of at least 3.0 mg or at least 830 international units (IU) of vitamin A as beta-carotene, more typically from 3.0 to 180 mg or 830 to 50,000 IU vitamin A as beta-carotene, most typically from about 7.2 to 108 mg or 2000 to 30,000 IU of vitamin A as beta-carotene is typically present for an adult dosage. In another example, a total amount of at least 3.0 mg or at least 10,000 international units (IU) of vitamin A as beta-carotene, more typically from 3.0 to 36 mg or 10,000 to 120,000 IU vitamin A as beta-carotene, most typically from about 7.5 to 21 mg or 25,000 to 70,000 IU of vitamin A as beta-carotene is typically present for an adult dosage.

Specific amounts of the vitamin A present in the composition may be dependent on the body weight of the mammal. In one specific example, the amount of vitamin A present as retinol in the composition is about 0.0178 mg/kg body weight. Thus, for an average human weighing about 70 kg, the amount of vitamin A present as retinol in the composition may be about 1.25 mg. If the vitamin A is in the form of beta-carotene, in one example, the beta carotene in the composition is about 0.257 mg/kg body weight may be present in an amount of about 18 mg. In another example, the beta-carotene in the composition may be about in an amount of about 15 mg.

It is to be appreciated that, when additional scavengers of singlet oxygen such as resveratrol are present in the composition in addition to vitamin A, the total amount of scavengers of singlet oxygen may be greater than the ranges set forth above for the at least one scavenger of singlet oxygen, so long as at least one scavenger of singlet oxygen is present in the amounts set forth above. In addition, other scavengers of singlet oxygen may be used in place of vitamin A, so long as the amount of the at least one scavenger of singlet oxygen is present within the amounts set forth above. When present, the resveratrol is typically included in the composition in an amount of at least 1 mg, more typically in an amount of from 10 mg to 1500 mg, most typically in an amount of from 15 mg to 1000 mg.

The at least one scavenger of singlet oxygen tends to prevent the initial formation of lipid peroxides while the donor antioxidant tends to reduce peroxyl radicals and inhibits propagation of lipid peroxidation that contributes to inner ear pathology. More specifically, the donor antioxidant reacts with and reduces peroxyl radicals and thus serves a chain-breaking function to inhibit propagation of lipid peroxidation. As is evident from the chain-breaking function of the donor antioxidant in lipid peroxidation, the donor antioxidant functions within cell membranes. A specific donor antioxidant that is contemplated for use in the composition of the subject disclosure is vitamin E. Vitamin E is a generic term for all tocols and tocotrienol derivatives with a biological activity of alpha-tocopherol. Primary dietary forms of vitamin E include vitamin E itself and alpha-tocopherol. Trolox®, a water-soluble analogue of alpha-tocopheral commercially available from Hoffman-Laroche, Ltd. of Basel, Switzerland, is a research agent that is typically used as a source of vitamin E.

The donor antioxidant is typically present in the composition, for example, in an amount of at least 75 IU, more typically from 75 IU to 2,000 IU, more typically from 150 to 1,500 IU, most typically from 150 IU to 800 IU. In another example, the donor antioxidant is present in the composition in an amount of at least 75 IU, more typically from 75 IU to 1,500 IU, most typically from 150 IU to 800 IU. As known in the art, a conversion of IU to weight for synthetic vitamin E is 0.66 mg/IU and for natural vitamin E is 0.45 mg/IU. Thus, when the donor antioxidant is synthetic vitamin E, in on example, at least 75 IU of vitamin E is equivalent to at least 50 mg of vitamin E, from 75 to 2,000 IU of synthetic vitamin E is equivalent to from 50 to 1,320 mg of vitamin E, from 150 to 1,500 IU of synthetic vitamin E is equivalent to from 100 to 1,000 mg of vitamin E, and from 150 to 800 IU of synthetic vitamin E is equivalent to from 100 to 536 mg of vitamin E. In another example, when the donor antioxidant is vitamin E, at least 75 IU of vitamin E is equivalent to at least 50 mg of vitamin E, from 75 to 1500 IU of vitamin E is equivalent to from 50 to 1000 mg of vitamin E, and from 150 to 800 IU of vitamin E is equivalent to from 150 to 600 mg of vitamin E. As with the amount and type of vitamin A, specific amounts of the vitamin E present in the composition may be dependent on the body weight of the mammal. In one specific example, the amount of synthetic vitamin E present in the composition is about 3.8 mg/kg body weight. Thus, for an average human weighing about 70 kg, the amount of vitamin E present in the composition may be about 266 mg. In another specific example, the amount of synthetic or natural vitamin E present in the composition is about 2.6 mg/kg body weight. Thus, for an average human weighing about 70 kg, the amount of vitamin E present in the composition may be about 182 mg.

In addition to the at least one scavenger of singlet oxygen and the donor antioxidant, the composition further includes the third antioxidant. While the third antioxidant may be a scavenger of singlet oxygen, the third antioxidant may also be an antioxidant that functions through a different mechanism. When the third antioxidant is a scavenger of singlet oxygen, the at least one scavenger of singlet oxygen is still present in the composition as a separate component from the third antioxidant, and is still present in the composition in the amounts set forth above for the at least one scavenger of singlet oxygen. As a result of the third antioxidant being another scavenger of singlet oxygen, the resulting composition would have at least two scavengers of singlet oxygen.

The third antioxidant is typically vitamin C, which is a scavenger of singlet oxygen and reactive nitrogen species. It is to be appreciated that, although the third antioxidant is typically vitamin C, other antioxidants may be used in place of the vitamin C, and the other antioxidants may function through different mechanisms than vitamin C. The term vitamin C applies to substances that possess antiscorbutic activity and includes two compounds and their salts: L-ascorbic acid (commonly called ascorbic acid) and L-dehydroascorbic acid. In addition to being known as ascorbic acid and L-ascorbic acid, vitamin C is also known as 2,3-didehydro-L-threo-hexano-1,4-lactone, 3-oxo-L-gulo-furanolactone, L-threo-hex-2-enonic acid gamma-lactone, L-3-keto-threo-hexuronic acid lactone, L-xylo-ascorbic acid and antiscorbutic vitamin. Vitamin C is known to scavenge both reactive oxygen species and reactive nitrogen species. It can be oxidized by most reactive oxygen and nitrogen species, including superoxide, hydroxyl, peroxyl and nitroxide radicals, as well as such non-radical reactive species as singlet oxygen, peroxynitrite and hypochlorite. Vitamin C thus inhibits lipid peroxidation, oxidative DNA damage, and oxidative protein damage.

In contrast to vitamin A, which functions best under conditions present in most tissues, water-soluble vitamin C is an excellent free radical scavenger in an aqueous phase to thus reduce free radicals at a site different from that of vitamin A. More specifically, ascorbic acid functions to reduce free radicals in fluid, such as in cytoplasmic fluid and/or blood, before the free radicals reach cell membranes.

The third antioxidant is typically present, for example, in an amount of at least 4,000 IU, more typically from 4,000 to 60,000, more typically from 8,000 to 40,000 IU, most typically from 8,000 to 20,000 IU. In another example, the third antioxidant is typically present in an amount of at least 4,000 IU, more typically from 6,000 to 40,000 IU, and most typically from 8,000 to 20,000 IU. Using vitamin C as an example for converting IU to weight units for the third antioxidant, as known in the art, a conversion of IU to weight for vitamin C is 0.05 mg/IU. Thus, at least 4,000 IU of vitamin C is equivalent to at least 200 mg of vitamin C, from 6,000 to 60,000 IU of vitamin C is equivalent to from 300 to 3,000 mg vitamin C, from 6,000 to 40,000 IU of vitamin C is equivalent to from 300 to 2,000 mg, from 8,000 to 40,000 IU of vitamin C is equivalent to from 400 to 2,000 mg vitamin C, and from 8,000 to 20,000 IU vitamin C is equivalent to from 400 to 1,000 mg vitamin C. As with vitamins A and E, specific amounts of the vitamin C or other third antioxidant present in the composition may be dependent on the body weight of the mammal. In one specific example, the amount of vitamin C present in the composition is about 7.14 mg/kg body weight. Thus, for an average human weighing about 70 kg, the amount of vitamin C present in the composition may be about 500 mg.

As set forth above, the composition further includes a vasodilator. Typically, the vasodilator includes magnesium; however, the vasodilator, for purposes of the subject disclosure, may include other vasodilators in place of or in addition to magnesium, in place of or in addition to those including magnesium, or may include only magnesium or only magnesium-containing compounds. Vasodilators can be used for treating cCMV induced hearing loss. Vasodilators including magnesium prevent decreases in cochlear blood flow and oxygenation via biochemical mechanisms involving changes in calcium concentration and prostaglandins. Deficient cochlear blood flow and lack of oxygenation can contribute to cCMV induced hearing loss by causing metabolic changes in lateral wall tissues important for maintaining normal homeostasis of the inner ear, e.g. endocochlear potential, and normal transduction; and may cause cell death in sensitive hair cells within a cochlea of the ear. Vasodilators including magnesium have also been found to improve the efficacy of immunosuppressant therapy or carbogen inhalation therapy in recovery from cCMV induced hearing loss. Furthermore, it has been found that magnesium deficiency leads to increased calcium channel permeability and greater influx of calcium into cochlear hair cells and afferent nerve endings, increased glutamate release, and auditory nerve excitotoxicity, each of which play a role in health of the inner ear. Although the vasodilators are known in the art for treating cCMV induced hearing loss, the vasodilators, especially those including magnesium, exhibit an unexpected additive effect when combined with the biologically effective amounts of the at least one scavenger of singlet oxygen, the donor antioxidant, and the third antioxidant, especially when the at least one scavenger of singlet oxygen is vitamin A, the donor antioxidant is vitamin E, and the third antioxidant is vitamin C for purposes of treating noise-induced cCMV induced hearing loss. The additive effect referred to above is greater than not only the most efficacious of the components for treating inner ear pathology that causes cCMV induced hearing loss, but typically greater than the sum of the effects of each of the components for treating cCMV induced hearing loss. While vasodilators other than those including magnesium are envisioned for purposes of the present disclosure, additive effects are not observed with all vasodilators. For example, betahistine, which is another known vasodilator, does not exhibit an additive effect.

The vasodilator including magnesium typically includes a magnesium salt or magnesium salt complex and, more specifically, magnesium sulfate or magnesium citrate. Other vasodilators including magnesium that may be suitable for purposes of the subject disclosure include; magnesium acetate, magnesium aspartate, magnesium carbonate, magnesium chloride, magnesium fumarate, magnesium gluconate, magnesium glycinate, magnesium hydroxide, magnesium lactate, magnesium oxide, magnesium salicylate, magnesium stearate, and magnesium sulfate. Other representative salts include but are not limited to; hydrobromide, hydrochloride, bisulfate, nitrate, arginate, ascorbate, oxalate, valerate, oleate, palmitate, laurate, borate, benzoate, phosphate, tosylate, maleate, fumarate, succinate, taurate, tartrate, naphthylate, mesylate, glucoheptonate, lactobionate and laurylsulphonate salts.

Typically, the vasodilator is present in the composition in an amount of at least 50 mg. For example, when the vasodilator is magnesium, the magnesium is typically present in an amount of from 50 to 450 mg, most typically from 100 to 350 mg. As with vitamins A, C, and E, specific amounts of the vasodilator present in the composition may be dependent on the body weight of the mammal. In one specific example, the amount of the vasodilator including magnesium present in the composition is about 4.46 mg/kg body weight. Thus, for an average human weighing about 70 kg, the amount of the vasodilator including magnesium present in the composition may be about 312 mg. In another example, the amount of the vasodilator including magnesium present in the composition is about 2.14 mg/kg body weight. Thus, for an average human weighing about 70 kg, the amount of the vasodilator including magnesium present in the composition may be about 150 mg.

Non-limiting examples of amounts of the typical components included in the composition, along with more and most typical amounts, are summarized in Table 1 below.

TABLE 1

| Component | | Amount | More Typical Amount | Most Typical Amount | Typical Dosage, mg/kg body weight |
|---|---|---|---|---|---|
| Vitamin A | | ≥830 IU | 830-10,000 IU | 2100-8,000 IU | 0.0178 mg/kg |
| | Vitamin A As beta-carotene | ≥830 IU | 830-50,000 IU | 2,000-30,000 IU | 0.257 mg/kg |
| Vitamin C | | ≥4,000 IU | 4,000-60,000 IU | 8,000-20,000 IU | 7.14 mg/kg |
| Vitamin E | | ≥75 IU | 75-2000 IU | 150-800 IU | 3.8 mg/kg (synthetic) |
| Magnesium | | ≥50 mg | 50-450 mg | 100-350 mg | 4.46 mg/kg |

With respect to Table 1, the amounts specified for the antioxidants and the vasodilator correlate, in terms of biological effectiveness, to amounts used for humans. Furthermore, it is to be appreciated that the biologically effective amounts of the antioxidants and vasodilator may be lower within the above ranges for children than for the average human, based on lower US recommended daily allowances and maximum intake levels for children. This is evident based on the typical dosages in Table 1 based on mg/kg.

Other non-limiting examples of amounts of the typical components included in the composition, along with more and most typical amounts, are summarized in Table 2 below.

TABLE 2

| Component | | Amount | More Typical Amount | Most Typical Amount | Typical Dosage, mg/kg body weight |
|---|---|---|---|---|---|
| Vitamin A | | ≥830 IU | 830-120,000 IU | 2,100-70,000 IU | — |
| | Vitamin A As Retinol | ≥830 IU | 830-50,000 IU | 2,100-5,900 IU | 0.0178 mg/kg |
| | Vitamin A As beta-carotene | ≥10,000 IU | 10,000-120,000 IU | 25,000-70,000 IU | 0.214 mg/kg |
| Vitamin C | | ≥4,000 IU | 6,000-40,000 IU | 8,000-20,000 IU | 7.14 mg/kg |
| Vitamin E | | ≥75 IU | 75-1,500 IU | 150-800 IU | 2.6 mg/kg |
| Magnesium | | ≥50 mg | 50-450 mg | 100-350 mg | 2.14 mg/kg |

With respect to Table 2, the amounts specified for the antioxidants and the vasodilator correlate, in terms of biological effectiveness, to amounts used in animal studies on guinea pigs. Furthermore, it is to be appreciated that the biologically effective amounts of the antioxidants and vasodilator may be lower within the above ranges for children than for the average human, based on lower U.S. recommended daily allowances and maximum intake levels for children. This is evident based on the typical dosages in Table 2 based on mg/kg.

In addition to the antioxidants and vasodilator, other components may also be present in the composition for treating cCMV induced hearing loss. These components may be used for treating the side effects of the antibiotic treatment also. For example, in one embodiment, the composition further includes a withanolide. Withanolides have been suggested for use in anti-inflammatory, anti-tumor, cytotoxic, and immunological applications. One example of a specific withanolide that may be included in the composition of the subject disclosure is the withanolide extracted from day lily plants. The extract is a powerful natural antioxidant which may be effective in preventing cell death in the inner ear by interrupting the cell-death pathway initiated by deafferentation of the auditory nerve. When included in the composition, the withanolide may be present in an amount of at least 10 ppm, more typically from 10 to 1000 ppm. Additional components, besides withanolides, can also be included. Typically, the composition is free of components that interfere with the biological mechanisms through which the at least one scavenger of singlet oxygen, the donor antioxidant, the third antioxidant, and the vasodilator function. The composition is also typically free of additional components that could degrade or neutralize the at least one scavenger of singlet oxygen, the donor antioxidant, the third antioxidant, and the vasodilator function when mixed therewith prior to internally administering the composition to the mammal. Those of skill in the art can readily identify such components in view of the mechanisms by which the individual components in the composition function as set forth above (e.g., components that cause vasoconstriction, various oxidizing agents, etc.).

It is also to be appreciated that, even if additional components are present in the composition that could interfere with the mechanisms by which the at least one scavenger of singlet oxygen, the donor antioxidant, the third antioxidant, and the vasodilator function, the composition described above is may still be effective for purposes of treating side effects of the antibiotic treatment. As one example, and as described in further detail below, the composition including the at least one scavenger of singlet oxygen, the donor antioxidant, the third antioxidant, and the vasodilator may be effective for treating cCMV induced hearing loss.

As alluded to above, the method of treating cCMV induced hearing loss includes the step of internally administering the composition of the subject disclosure to a mammal. The composition may be orally administered to the mammal, such as in the form of a tablet, liquid, gel, etc. Alternatively, the composition may be intravenously administered to the mammal through an IV or an injection of the composition.

For purposes of the subject disclosure, cCMV is typically associated with hearing loss as objectively measured in terms of differences in threshold shift, or through measurement of a percentage of hair cell loss. In mouse studies, cCMV induced hearing loss, as objectively measured as a change in auditory brainstem response or distortion product otoacoustic emission thresholds, is observed in the majority of animals, either transiently or prolonged, following inoculation. Reduction in cCMV induced hearing loss reflecting the efficacy of the composition for treating cCMV induced hearing loss may be measured as an average difference in threshold shift from baseline threshold sensitivity at 8, 16, and 32 kHz, as compared to an untreated control, after intracerebral inoculation with murine cCMV. Small differences in threshold shift may be associated with less cCMV induced hearing loss and greater efficacy of the composition for treating the cCMV induced hearing loss.

It is has been shown that hair cell loss correlates to threshold shift. For example, in guinea pig ears that recover from temporary threshold shift, morphological damage is limited to tips of stereocilia in a third row of outer hair cells (OHCs) whereas ears from animals with permanent threshold shift have damage to all three rows of OHCs and, in some cases, the inner hair cells (IHCs), with damage throughout the length of the stereocilia as well as the to the body of the hair cell.

In one embodiment, the composition of the present disclosure is administered systemically to the mammal within one day of inoculation in order to alleviate permanent threshold shift. It is to be appreciated that by administering the composition within one day of inoculation, treatment prior to inoculation is also contemplated through the method of the present disclosure.

Treatment within one day is most appropriate when the mammal has sustained infection to the inner ear. Ideally, the composition is administered to the mammal prior to inoculation to the inner ear. An alternative treatment would be administration in a cCMV infected child with initial normal hearing or hearing impairment to prevent future progressive hearing loss. For example, the composition may be administered after the child is diagnosed with cCMV.

After initial administration of the composition, the composition is typically administered to the mammal each day for at least seven days following the inoculation. Although excellent results have been achieved through such treatment, it is to be appreciated that other treatment regimens may also prove efficacious for purposes of the present disclosure.

In one embodiment, the composition is administered after peroxyl radical formation, which may be further defined as oxidative DNA damage and/or oxidative protein damage. In another embodiment, the composition is administered after peroxidation in the mammal and/or after formation of lipid peroxyl radicals within a lipophilic compartment of a mitochondrial membrane in the mammal. In a further embodiment, the composition is administered after vasoconstriction of blood vessels in an ear of the mammal. In still another embodiment, the composition is administered after formation of lipid peroxyl radicals within a lipophilic compartment of a mitochondrial membrane in the mammal.

EXAMPLES

To address whether Nrf2 deficiency causes susceptibility to cCMV-induced hearing loss, Nrf2−/− mice with C57BL/6 genetic background were infected with 200 pfu cCMV by intracerebral injection on post-natal day 3. Statistically significant worsening of hearing thresholds in cCMV infected Nrf2−/− mice is observed using auditory brainstem response and distortion product otoacoustic emission testing when compared to uninfected Nrf2−/− mice. Evidence of excessive ROS production is also detected using a superoxide-sensitive fluorescent probe dihydroethidium (DHE) on unfixed cochlear cryosectioned specimens. In these experiments, increased DHE fluorescence in the spiral ganglion of cCMV infected Balb/c mice 7 days after inoculation is demonstrated when compared to uninfected Balb/c mice.

Mice were administered ACE-Mg for 7 days following cCMV infection and tested for auditory function at one month of age. An amelioration of hearing loss in the ACE-Mg treated cCMV infected groups was observed when compared to untreated cCMV infected mice.

To assess the magnitude of cochlear damage caused by cCMV and whether pretreatment with ACE-Mg provides a protective effect on cochlear morphology, scanning electron microscopy (SEM) was performed on cochlear whole mounts at P30. There was a significant difference between the cCMV untreated mice and specimens from the uninfected control, and cCMV+ACE-Mg groups. In the uninfected cochlea (control), there are normally three well-defined rows of outer hair cells across the length of the basilar membrane. cCMV-infected mice exhibited substantial outer hair cell loss in the basal and apical turns of the organ of Corti. Treatment with ACE-Mg administration resulted in significantly less outer hair cell loss in all cochlear turns. These data suggest that ACE-Mg treatment produced significant partial protection of outer hair cell from cCMV infection.

All combinations of the aforementioned embodiments throughout the entire disclosure are hereby expressly contemplated in one or more non-limiting embodiments even if such a disclosure is not described verbatim in a single paragraph or section above. In other words, an expressly contemplated embodiment may include any one or more elements described above selected and combined from any portion of the disclosure.

One or more of the values described above may vary by ±5%, ±10%, ±15%, ±20%, ±25%, etc. Unexpected results may be obtained from each member of a Markush group independent from all other members. Each member may be relied upon individually and or in combination and provides adequate support for specific embodiments within the scope of the appended claims. The subject matter of all combinations of independent and dependent claims, both singly and multiply dependent, is herein expressly contemplated. The disclosure is illustrative including words of description rather than of limitation. Many modifications and variations of the present disclosure are possible in light of the above teachings, and the disclosure may be practiced otherwise than as specifically described herein.

It is also to be understood that any ranges and subranges relied upon in describing various embodiments of the present disclosure independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present disclosure, and such ranges and subranges may be further delineated into relevant halves, thirds, quarters, fifths, and so on. As just one example, a range "of from 0.1 to 0.9" may be further delineated into a lower third, i.e. from 0.1 to 0.3, a middle third, i.e. from 0.4 to 0.6, and an upper third, i.e. from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

What is claimed is:

1. A method of treating congenital cytomegalovirus induced hearing loss, said method comprising the step of internally administering a composition to the mammal, wherein the composition consists essentially of a biologically effective amount of vitamin A, vitamin E, vitamin C, a vasodilator comprising magnesium, and, optionally, a withanolide, and/or resveratrol.

2. A method as set forth in claim 1 wherein the step of internally administering the composition is further defined as orally administering the composition to the mammal.

3. A method as set forth in claim 1 wherein the step of internally administering the composition is further defined as intravenously administering the composition to the mammal.

4. A method as set forth in claim 1 further comprising the step of detecting congenital cytomegalovirus induced hearing loss in a mammal.

5. A method as set forth in claim 4 wherein the step of internally administering the composition occurs prior to the step of detecting the congenital cytomegalovirus induced hearing loss in the mammal.

6. A method as set forth in claim 5 wherein reduction in congenital cytomegalovirus induced hearing loss is measured as an average difference in threshold shift from baseline threshold sensitivity at 8, 16, and 32 kHz, as compared to an untreated control, after intracerebral inoculation with murine congenital cytomegalovirus.

7. A method as set forth in claim 1 wherein the composition further comprises resveratrol.

8. A method as set forth in claim 1 wherein the vitamin A is present in the composition in an amount of at least 830 IU.

9. A method as set forth in claim 1 wherein the vitamin C is present in the composition in an amount of at least 4,000 IU.

10. A method as set forth in claim 1 wherein the vitamin E is further defined as a water-soluble analogue of alpha-tocopheral.

11. A method as set forth in claim 1 wherein the vitamin E is present in the composition in an amount of at least 75 IU.

12. A method as set forth in claim 1 wherein the composition further comprises the withanolide.

13. A method as set forth in claim 1 wherein the vasodilator is present in an amount of at least 50 mg.

14. A method as set forth in claim 1 wherein the composition provides an additive effect that is equal to or greater than a sum of the effects of the individual components.

15. A method of treating congenital cytomegalovirus induced hearing loss, said method comprising the step of internally administering a composition to the mammal, wherein the composition consists essentially of a biologically effective amount of vitamin A, vitamin E, vitamin C, a vasodilator comprising magnesium, and, optionally, a withanolide, and/or resveratrol, and wherein the composition is administered after peroxyl radical formation.

16. A method as set forth in claim 15 wherein the formation of peroxyl radicals is further defined as oxidative DNA damage.

17. A method as set forth in claim 15 wherein the formation of peroxyl radicals is further defined as oxidative protein damage.

18. A method as set forth in claim 15 wherein the composition provides an additive effect that is equal to or greater than a sum of the effects of the individual components.

19. A method of treating congenital cytomegalovirus induced hearing loss, said method comprising the step of internally administering a composition to the mammal, wherein the composition consists essentially of a biologically effective amount of vitamin A, vitamin E, vitamin C, a vasodilator comprising magnesium, and, optionally, a withanolide, and/or resveratrol, and wherein the composition is administered after lipid peroxidation in the mammal.

20. A method as set forth in claim 19 wherein the composition provides an additive effect that is equal to or greater than a sum of the effects of the individual components.

21. A method of treating congenital cytomegalovirus induced hearing loss, said method comprising the step of internally administering a composition to the mammal, wherein the composition consists essentially of a biologically effective amount of vitamin A, vitamin E, vitamin C, a vasodilator comprising magnesium, and, optionally, a withanolide, and/or resveratrol, and wherein the composition is administered after vasoconstriction of blood vessels in an ear of the mammal.

22. A method as set forth in claim 21 wherein the composition provides an additive effect that is equal to or greater than a sum of the effects of the individual components.

23. A method of treating congenital cytomegalovirus induced hearing loss, said method comprising the step of internally administering a composition to the mammal, wherein the composition consists essentially of a biologically effective amount of vitamin A, vitamin E, vitamin C, a vasodilator comprising magnesium, and, optionally, a withanolide, and/or resveratrol, and wherein the composition is administered after formation of lipid peroxyl radicals within a lipophilic compartment of a mitochondrial membrane in the mammal.

24. A method as set forth in claim 23 wherein the composition provides an additive effect that is equal to or greater than a sum of the effects of the individual components.

* * * * *